United States Patent
Komuro et al.

(10) Patent No.: US 7,432,387 B2
(45) Date of Patent: Oct. 7, 2008

(54) PROCESS FOR PRODUCING ORGANOSILICON COMPOUND

(75) Inventors: Katsuhiko Komuro, Utsunomiya (JP); Hiroshi Suzuki, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 11/572,503

(22) PCT Filed: Aug. 24, 2004

(86) PCT No.: PCT/JP2004/012116

§ 371 (c)(1),
(2), (4) Date: Jan. 23, 2007

(87) PCT Pub. No.: WO2006/021989

PCT Pub. Date: Mar. 2, 2006

(65) Prior Publication Data

US 2008/0051594 A1    Feb. 28, 2008

(51) Int. Cl.
*C07F 7/02*    (2006.01)
(52) U.S. Cl. ...................................... 556/449
(58) Field of Classification Search ........................ None
See application file for complete search history.

(56) References Cited

FOREIGN PATENT DOCUMENTS

| JP | 05-171114 | 7/1993 |
|---|---|---|
| JP | 2001/005185 | 1/2001 |
| JP | 2002-055456 | 2/2002 |
| JP | 2002-179795 | 6/2002 |
| JP | 2002-338583 | 11/2002 |
| JP | 2004-295104 | 10/2004 |

*Primary Examiner*—Samuel A Barts
(74) *Attorney, Agent, or Firm*—Oblon, Spivak, McClelland, Maier & Neustadt, P.C.

(57) ABSTRACT

[Problems] It is to provide a process by which an organosilicon compound having a hexafluorocarbinol group can be easily produced on an industrial scale without via a complicated production step.

[Means for solving problems] The following compound represented by the formula (1) and a trialkoxysilane are subjected to hydrosilylation to obtain a compound represented by the formula (2). (In the formula, R is an alkoxy group having carbon atoms from 1 to 3.)

[Effects] Since the compound obtained in the present invention is a trifunctional alkoxysilane, use of a crosslinking reaction leads to a silicone resin and a silsesquioxane. The hexafluorocarbinol group functions as an excellent alkaline water-soluble group.

7 Claims, 1 Drawing Sheet

PROCESS FOR PRODUCING ORGANOSILICON COMPOUND

TECHNICAL FIELD

The present invention relates to a method for producing a trialkoxysilane having a hexafluorocarbinol group.

BACKGROUND ART

Various compounds are known as alkoxysilanes that have a phenol group or a catechol group. Organosilicon resins prepared with these alkoxysilanes have excellent alkali-solubility and are used as additives to resins, electronic materials and various reactable base materials (cvf. Patent Document 1, Patent Document 2). However, each of these resins has a phenol group and therefore absorbs ultraviolet radiation. Because of the absorption, the resins are problematic with respect to important qualities including transparency, weatherability, microfabricating ability and the like.

Recently, a variety of alkali-soluble resins have developed and an organosilicon resin in which a carboxyl group is introduced is reported (cf. Patent Document 3).

However, it is difficult to obtain an excellent alkali-solubility by using these organosilicon resins having a carboxyl group comparable to the case of a phenol group. An improvement of the alkali-solubility has been desired. A hexafluorocarbinol group a has almost the same pKa (9.82) as phenol and possesses an excellent alkali-solubility. Therefore, an organosilicon compound containing a hexafluorocarbinol group is receiving increased attention.

Trichlorosilane wherein a hexafluorocarbinol group has been protected by an organic group is so far known (cf. Patent Document 4). The reaction for obtaining this compound is a hydrosilylation reaction in which a compound having a hexafluorocarbinol group and a carbon-carbon unsaturated group, and trichlorosilane are starting materials. The reason why a starting material wherein a hexafluorocarbinol group has been protected by an organic group is used in this reaction is to prevent from reacting a chlorosilyl group of the chlorosilane as another starting material and a hexafluorocarbinol group.

In the above-mentioned production process using trichlorosilane as a starting material, since a compound having a hexafluorocarbinol group can be obtained when a de-protecting step of a hexafluorocarbinol group is performed after hydrosilylating, there is a problem leading to a complicated production step.

[Patent Document 1] JP-A-2002-179795
[Patent Document 2] JP-A-2002-338583
[Patent Document 3] JP-A-2001-005185
[Patent Document 4] JP-A-2002-55456

DISCLOSURE OF THE INVENTION

[Problems to be Solved by the Invention]

An object of the present invention is to provide a process by which an organosilicon compound having a hexafluorocarbinol group can be easily produced on an industrial scale without via a complicated production step.

[Means for Solving Problems]

The present inventors have made earnest investigations and found out that when a trialkoxysilane was used as a starting material, an organosilicon compound having a hexafluorocarbinol group was produced by one step reaction because an alkoxysilyl group and a hexafluorocarbinol group were not reacted, to complete the present invention.

That is, the present invention is a method for producing an organosilicon compound that is characterized in that the following compound (1) and a trialkoxysilane are subjected to hydrosilylation to obtain a compound (2).

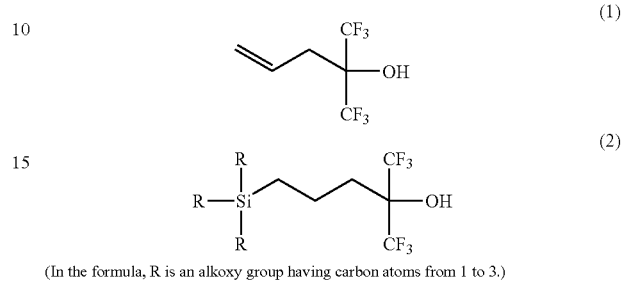

(In the formula, R is an alkoxy group having carbon atoms from 1 to 3.)

[Effects of the Invention]

According to the present invention, a trialkoxysilane having a hexafluorocarbinol group can be produced by one step reaction.

The producing method of the present invention is useful for industrial producing method for a trialkoxysilane having a hexafluorocarbinol group.

The HFC organosilicon compound has a hydrolysable trialkoxy group bonded to a silicon atom, therefore a reaction with other organosilicon compound (including polymer) gives a siloxane bond and leads to a coupling reaction with a silanol group in an inorganic compound. In addition, being trifunctional alkoxysilane, use of a crosslinking reaction leads to a silicone resin and a silsesquioxane. On the other hand, the hexafluorocarbinol group functions as an excellent alkaline water-soluble group.

The HFC organosilicon compound is useful for an intermediate raw material in organic synthesis, a starting material for synthesizing polymer resins, a modifying agent for polymers, a surface-treating agent for inorganic compounds and a coupling agent for a variety of materials.

BEST MODE FOR CARRYING OUT THE INVENTION

Figure 1:
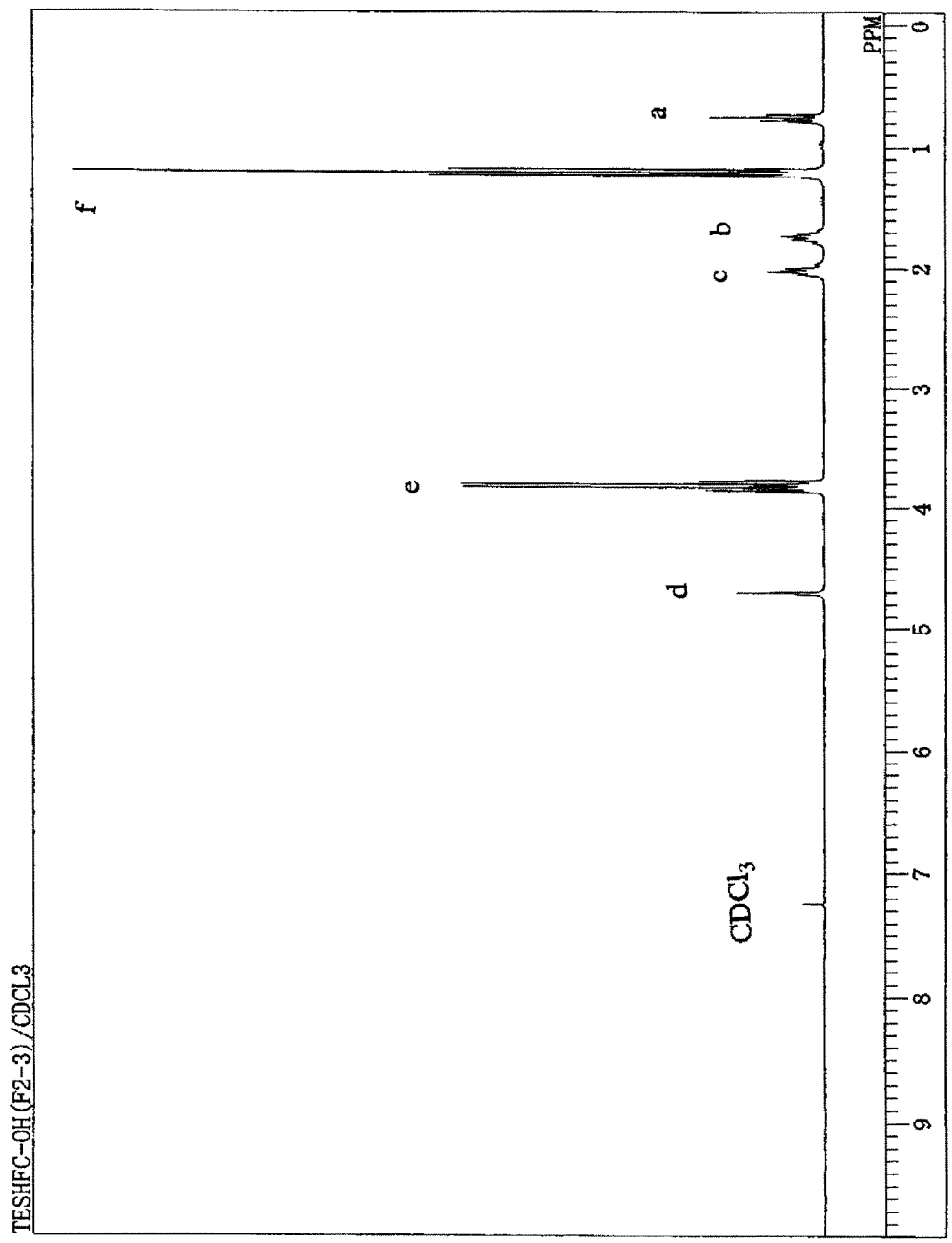
FIG. 1 is $^1$H-NMR spectrum of the compound obtained in Example 1.

Hereinafter, the present invention will be described in detail.

In the organosilicon compound obtained by the present invention (hereinafter, referred to as HFC organosilicon compound), R is an alkoxy group having carbon atoms from 1 to 3. The preferable specified example includes methoxy group, ethoxy group and propyloxy group. The propyloxy group may be linear or branched. Among these, ethoxy group is generally preferable as R, since it is easy to obtain the raw material and to synthesize.

The preferable specified example of the HFC organosilicon compound is the compound (3) represented by the following structural formula.

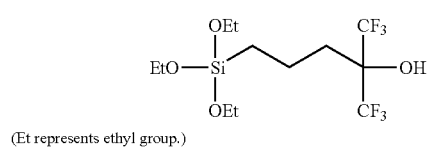

(Et represents ethyl group.)

The HFC organosilicon compound can be obtained by conducting hydrosilylation of the above compound (1) and a trialkoxysilane.

The preferable charging ratio for reacting these starting materials is that trialkoxysilane is used by 10-20 mol % more than the above compound (1).

In the case of producing the above compound (3), the compound (1) is subjected to reaction with triethoxysilane. This reaction is ordinarily performed in the presence of a catalyst. The preferable catalyst includes a simple substance, an organic metal complex, a metal salt, a metal oxide and the like of groups VIII-X metal such as cobalt, nickel, ruthenium, rhodium, palladium, iridium and platinum. In general, a platinum-based catalyst is used.

The preferable platinum-based catalyst includes platinic chloride hexahydrate ($H_2PtCl_6 \cdot 6H_2O$), cis-$PtCl_2(PhCN)_2$, platinum carbon, platinum complex in which divinyltetramethyldisiloxane is coordinated (PtDVTMDS), and the like. Ph represents phenyl group. The preferable amount to be added of the catalyst is in the range from 0.1 to 1,000 ppm based on the amount of the compound (1).

Additionally, the reaction temperature is not particularly limited since it depends on a heating process from outside of the reaction system and a supplying rate of triethoxysilane. However, when the reaction temperature is holding a range from room temperature to 110° C., the hydrosilylation can be smoothly progressed. After the reaction, a solvent and a volatile component is eliminated under a reduced pressure and rectified by vacuum distillation to obtain the compound (3).

In the HFC organosilicon compound, a functional group can be easily introduced by using a chlorosilane and the HFC organosilicon compound is also useful for an intermediate in organic systhesis. The preferable chlorosilane includes trimethylchlorosilane and the like. The preferable base used for the reaction with the chlorosilane includes triethylamine, diisopropylethylamine, pyridine, potassium hydroxide, sodium hydroxide and the like. The preferable solvent includes an ether such as diethylether, diisopropylether and THF, a polar solvent such as dichloromethane, chloroform, pyridine, DMF and DMSO, and the like.

EXAMPLES

Hereinafter, the present invention will be described in detail using Reference Example and Example.

Example 1

The inside of a reactor provided with a stirrer, a thermometer and a condenser was controlled to an atmosphere of dry nitrogen. 50.0 g (240 mmol) of the compound (1) and 47.3 g (288 mmol) of triethoxysilane were charged into the reactor and heated by an oil bath while stirring. When the internal temperature reached 80° C., a xylene solution containing PtDVTMDS as a platinum catalyst (124 μL, 0.012 mmol) was placed into the system. After dropping of the catalyst, stirring at 80° C. was conducted for 7 hours and left. Subsequently, a volatile component was eliminated under reduced pressure to purify the target compound by vacuum distillation (68.3 g, 76%).

When $^1$H-NMR measurement at 270 MHz was performed for this liquid, the spectrum shown in FIG. 1 was obtained. The d values and identifiers thereof were as shown in Table 1. The liquid thus obtained was confirmed as a trialkoxysilane having hexafluorocarbinol group (3).

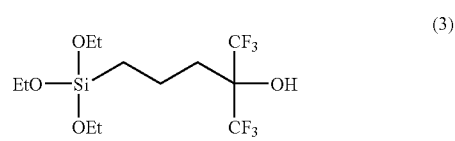

TABLE 1

| Measurement Method | d (ppm) | Identifier |
|---|---|---|
| NMR | 0.8 | a) |
|  | 1.2 | f) |
|  | 1.7 | b) |
|  | 2.0 | c) |
|  | 3.8 | e) |
|  | 4.7 | d) |

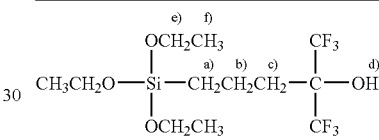

Reference Example

The inside of a reactor provided with a stirrer, a thermometer and a condenser was controlled to an atmosphere of dry nitrogen. 41.3 g (111 mmol) of the compound (3), 13.2 g (122 mmol) of trimethylchlorosilane and 100 g of methylene chloride were charged into the reactor and then 12.3 g (122 mmol) of triethylamine was slowly dropped while stirring. Stirring was performed at room temperature for 24 hours. A salt formed was filtered and a solvent was eliminated under reduced pressure to obtain a colorless and transparent liquid (44.4 g, 90%).

When $^1$H-NMR measurement at 270 MHz was performed for this liquid, the d values and identifiers thereof were as shown in Table 2. The liquid thus obtained was confirmed as a trialkoxysilane having hexafluorocarbinol group (4).

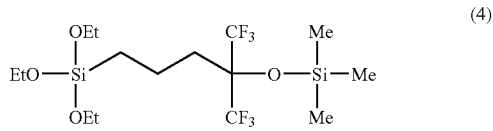

TABLE 2

| Measurement Method | d (ppm) | Identifier |
|---|---|---|
| NMR | 0.2 | d) |
|  | 0.8 | a) |
|  | 1.2 | f) |
|  | 1.7 | b) |

TABLE 2-continued

| Measurement Method | d (ppm) | Identifier |
|---|---|---|
| | 2.1 | c) |
| | 3.8 | e) |

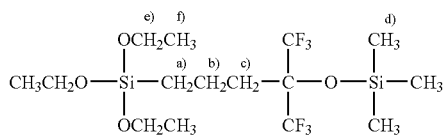

INDUSTRIAL APPLICABILITY

Since the organosilicon compound obtained by the present invention has an alkali-soluble hexafluorocarbinol group and three siloxane-bond-forming groups, it is useful for a starting material for synthesis of a variety of polymers, a modifying agent for polymers, a surface-treating agent for inorganic compounds and the like.

The invention claimed is:

1. A method for producing an organosilicon compound, comprising:
hydrosilylating compound of formula (1) with a trialkoxysilane compound, thereby producing a compound of formula (2)

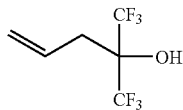

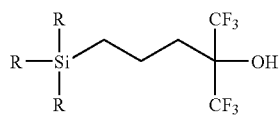

wherein R is a $C_{1-3}$ alkoxy group.

2. The process according to claim 1, wherein R is ethoxy.

3. The process according to claim 1, wherein said trialkoxysilane is present in the reaction in an amount of 10-20 mol % excess relative to compound (1).

4. The process according to claim 1, wherein the hydrosilation reaction is conducted in the presence of a catalyst.

5. The process according to claim 4, wherein the catalyst is an organometal, metal salt or metal oxide of a Group VIII to X metal.

6. The process according to claim 5, wherein the metal is cobalt, nickel, ruthenium, rhodium, palladium, iridium or platinum.

7. The process according to claim 4, wherein the catalyst is present in the reaction in an amount of 0.1 to 1,000 ppm based on the amount of compound (1).

* * * * *